United States Patent
Phillips

(10) Patent No.: US 6,254,547 B1
(45) Date of Patent: Jul. 3, 2001

(54) BREATH METHYLATED ALKANE CONTOUR: A NEW MARKER OF OXIDATIVE STRESS AND DISEASE

(76) Inventor: Michael Phillips, 1 Horizon Rd., Fort Lee, NJ (US) 07024

( * ) Notice: Subject to any disclaimer, the term of this patent is extended or adjusted under 35 U.S.C. 154(b) by 0 days.

(21) Appl. No.: 09/436,798

(22) Filed: Nov. 8, 1999

(51) Int. Cl.[7] .............. A61B 5/08; G01N 33/48
(52) U.S. Cl. ............. 600/532; 600/543; 600/529; 436/64; 436/813; 436/900
(58) Field of Search .............. 600/529, 532–533, 600/537, 538, 540, 541, 543; 436/64, 813, 900

(56) References Cited

U.S. PATENT DOCUMENTS 5,996,586 * 12/1999 Phillips .................. 436/64

* cited by examiner

*Primary Examiner*—Eric F. Winakur
*Assistant Examiner*—Navin Natnithithadha
(74) *Attorney, Agent, or Firm*—Pitney, Hardin, Kipp & Szuch, LLP

(57) ABSTRACT

The alkane profile, comprising the alveolar gradients of n-alkanes in breath having 2 to 20 carbons, and the alveolar gradients of methylated C3–C20 alkanes, is determined for the diagnosis of disease in mammals, including humans.

2 Claims, 13 Drawing Sheets

BREATH METHYLATED ALKANE CONTOUR: A NEW MARKER OF OXIDATIVE STRESS AND DISEASE

RELATED APPLICATIONS

The subject matter of pending U.S. application Ser. No. 09/229,020 filed on Jan. 12, 1999, is incorporated herein by reference.

FIELD OF THE INVENTION

The invention relates to the diagnosis of disease in mammals and more particularly to a method employing breath testing for the detection of particular diseases in humans.

BACKGROUND OF THE INVENTION

Reactive oxygen species (ROS) are toxic byproducts of energy production in the mitochondria. "Oxidative stress" is the constant barrage of oxidative damage which ROS inflict upon DNA, proteins, lipids and other biologically important molecules (1,2) (FIG. 1). Oxidative stress has been implicated as a pathologic mechanism in aging and several diseases (3,4,5). Consequently, oxygen is now recognized as both beneficial and harmful: it is essential to sustain mammalian life because it is the final acceptor of electrons in oxidative metabolism, but in this process it also causes oxidative stress and tissue damage.

Although the significance of oxidative stress in disease is well recognized, it has proved difficult to measure its intensity in vivo. Various markers have been proposed, including malonaldehyde and conjugated dienes in the blood, and hydrocarbons and hydrogen peroxide in the breath (6,7). Breath markers of oxidative stress have attracted attention because breath tests are intrinsically non-invasive and painless (8). Increased breath alkanes, particularly ethane and pentane, have demonstrated increased oxidative stress in breast cancer (9), rheumatoid arthritis (10), heart transplant rejection (11), acute myocardial infarction (12), schizophrenia (13) and bronchial asthma (14).

However, breath tests for ethane and pentane have limited value in screening for these disorders because their sensitivity and specificity are poor, resulting in large numbers of false positive and false negative results.

Oxidative stress produces many different degradation products, so that ethane and pentane are only one-dimensional markers of a larger process. Phillips et al recently reported a two-dimensional marker of oxidative stress, the breath alkane profile (U.S. application Ser. No. 09/229,020: A breath test for the detection of various diseases). This marker comprises the alveolar gradient (concentration in breath minus concentration in air) of a spectrum of alkanes from C4 to C20. The alveolar gradient varies with the difference between the rate of synthesis and the rate of clearance of a volatile organic compound (VOC) in the body. In a group of normal humans, the breath alkane profile was found to rise significantly with age.

Phillips et al also previously observed that methylated alkanes are common components of the breath in normal humans as well as in those suffering from lung cancer (15,16). These VOCs appeared to provide additional markers of oxidative stress.

SUMMARY OF THE INVENTION

A new marker of oxygen free radical (OFR) activity in the body was developed: the breath alkane profile. This comprised the alveolar gradients of a wide spectrum of VOCs ranging from C2 to C20 alkanes plotted as a function of carbon chain length. Similar profiles were developed for two alkane metabolites in breath: alkyl alcohols and 2-methyl alkanes. These profiles provide a new and non-invasive probe of human metabolism by demonstrating the relative predominance of synthesis versus clearance of a VOC in vivo. In the present inventive method, methylated alkanes were combined with the breath alkane profile in order to construct the breath methylated alkane contour (BMAC), a new three-dimensional marker of oxidative stress.

This technique has been refined herein by determining the alveolar gradient of methylated alkanes and incorporating this data into a three dimensional plot. That is, where alveolar gradient versus the carbon chain length of n-alkanes was previously plotted, a third dimension has been added to the plot, which is the location of methylation along the carbon chain of the n-alkane. The information obtained from identifying the methylation site, in addition to the alveolar gradient and the carbon chain length of the n-alkane, has produced a new and uniquely sensitive marker of oxidative stress in humans. In the data presented herein, collected in tests upon normal human beings and in those suffering form heart transplant rejection, it is shown that 1. Oxidative stress was greater in heart transplant recipients than in age-matched normal controls;
2. Oxidative stress increased with the severity of heart transplant rejection; and
3. The breath test was sensitive and specific for clinically significant rejection.

DETAILED DESCRIPTION OF THE PREFERRED EMBODIMENT

Figure 1:
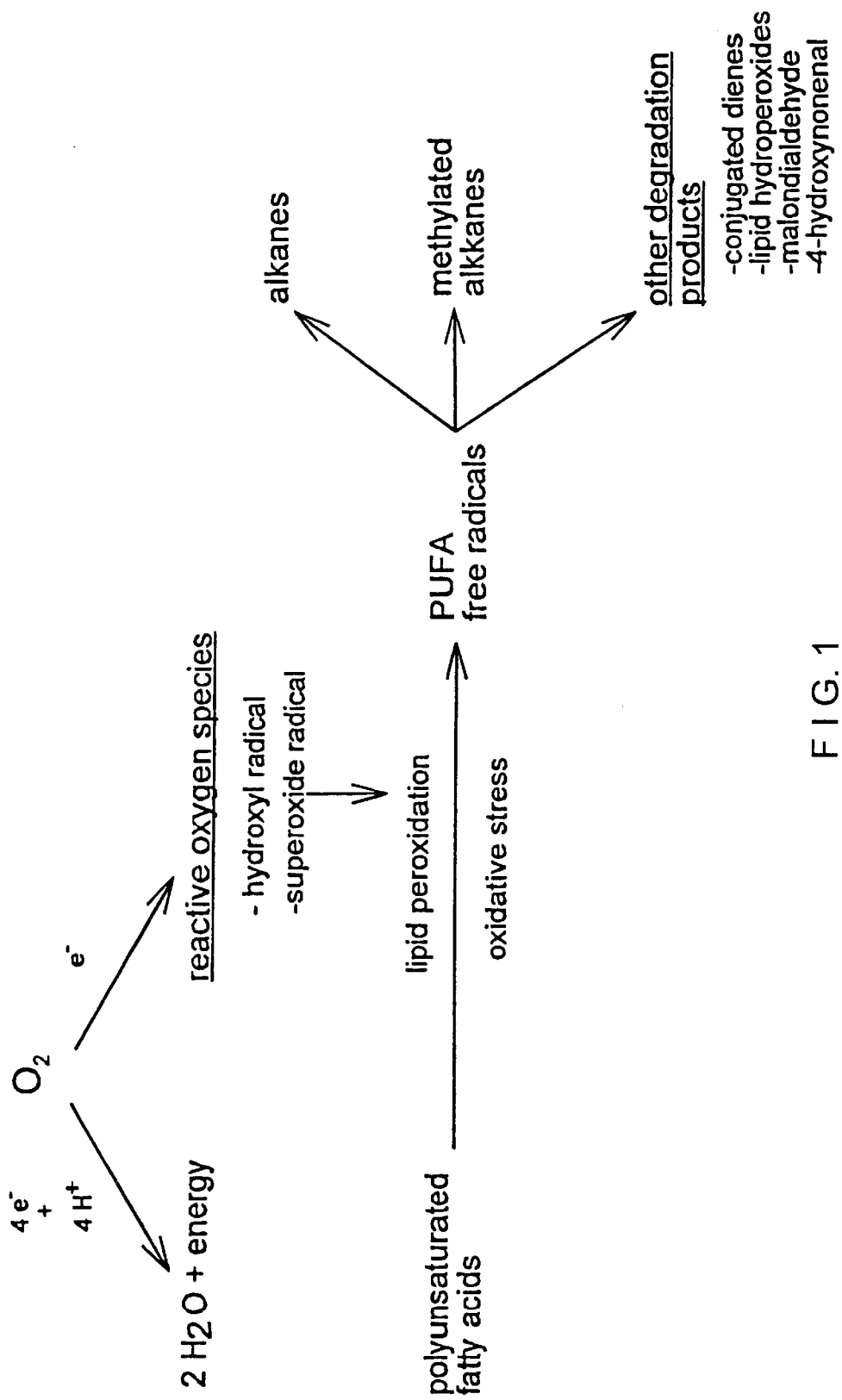
FIG. 1: Origin of oxidative stress and the generation of metabolic markers

The Breath Methylated Alkane Contour in Normal Humans

Collection of breath and air samples: The method has been described in reference nos. 16, 17, U.S. Pat. No. 5,465,728 entitled "Breath Collection," and U.S. application Ser. No. 09/229,020 entitled "A Breath Test for the Detection of Various Diseases," all incorporated herein by reference. VOC's in breath and room air were collected with a breath collection apparatus (BCA), a portable microprocessor-controlled device. Subjects wore a nose clip while inspiring and expiring through a low-resistance disposable mouthpiece into a wide bore breath reservoir (1.0 inch dia) open to the atmosphere at its distal end. The breath reservoir was heated in order to prevent condensation of water. Alveolar breath was pumped from the breath reservoir through a sorbent trap where the breath VOCs were captured on activated carbon (200 mg Carbotrap C (20/40 mesh) and 200 mg Carbopack B (60/80 mesh) (Supelco, Inc, Bellefonte, Pa.). The geometry of the system ensured that the sample comprised alveolar breath virtually uncontaminated by dead-space air. The collection period was 2.0 min at 0.5 l/min, and VOCs in two separate 1.0 l samples were collected: one of breath, and one of background room air.

Breath VOC assay: The method has been described in references 16 and 17 incoporated herein by reference. VOC's were desorbed from the sorbent trap heating it to 300° C. in an automated thermal desorber (ATD 400, Perkin Elmer, Norwalk, Conn., USA). A stream of helium flushed the VOC's onto a concentrator, a refrigerated sorbent trap maintained at 0° C. The concentrated sample of VOC's was then heated to 300° C., and the volatilized VOC's were separated by gas chromatography (GC), and identified and quantified by mass spectroscopy (MS).

Human subjects: Breath samples were collected between 7.00 am and 12.00 noon from 99 normal volunteers aged from 9 to 89 who had fasted from the previous midnight. Subjects sat for approximately 30 min prior to the collections of breath and air in order to allow time for equilibration between VOC's in room air and in the blood. Human research was approved by the institutional review board of St. Vincent's Medical Center, Staten Island, NY.

Analysis of data: The relative abundance of each alkane (C4 to C20) and its methylated derivatives were determined by the ratio of its chromatographic area under the curve (AUC) to the AUC of internal standard (0.25 ml 2 ppm 1-bromo-4-fluoro-benzene, Supelco). The alveolar gradient of each VOC was determined as the abundance in alveolar breath minus the abundance in room air. In each subject, a three dimensional breath methylated alkane contour (BMAC) was constructed by plotting the carbon skeleton length (x-axis) versus the methylation site (z-axis) versus the alveolar gradient (y-axis).

Results

The median age was used to split the group into younger and older halves (younger half: n=49, range 9–40, mean=30.3 years; older half: n=50, range 40–89, mean=68.3 year; $p<0.0001$).

Figure 2:
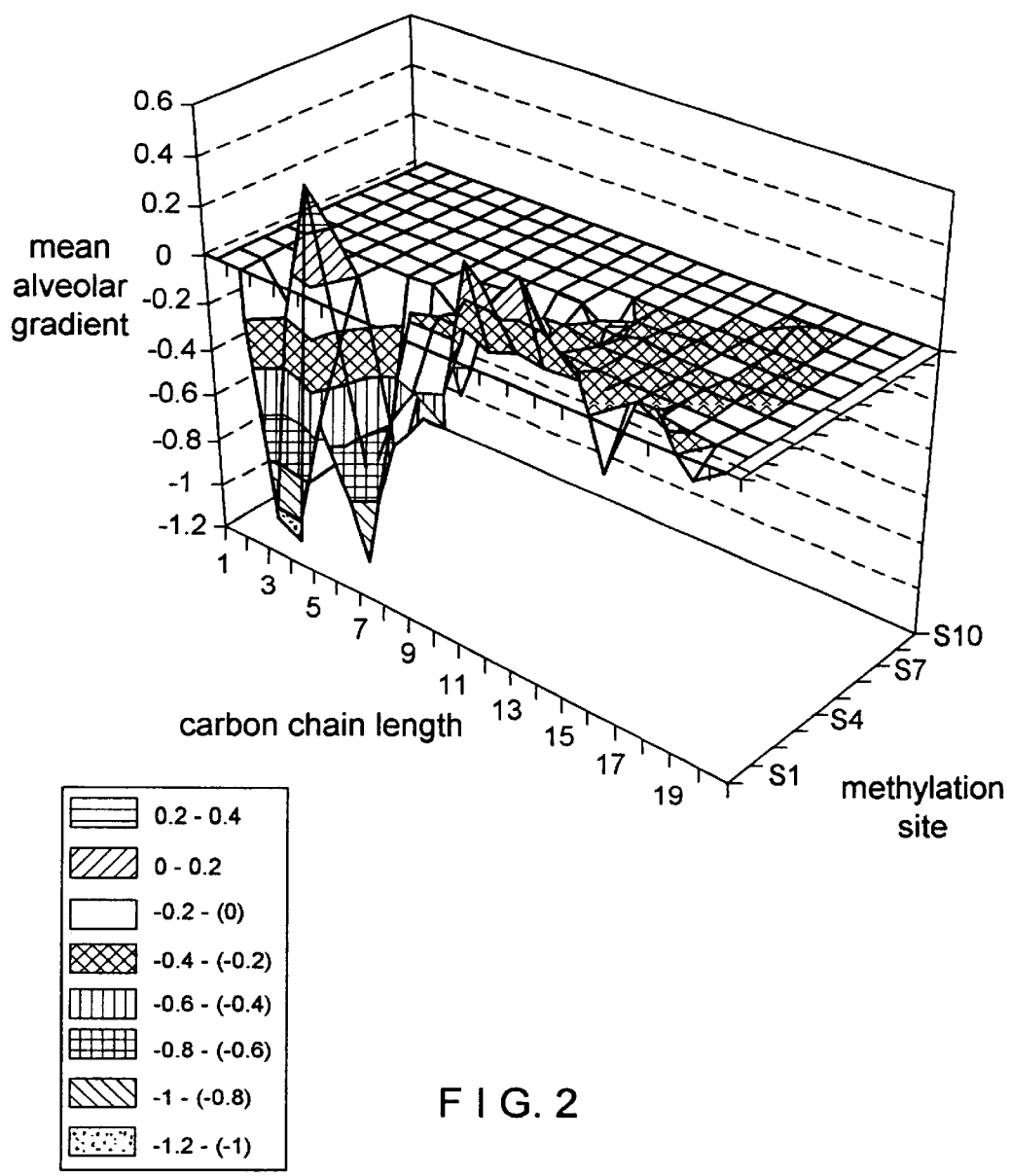
FIG. 2: Breath methylated alkane contour—mean of 99 normal subjects. Note that this figure also includes n-alkanes as methylated at C1. For example an alkane with carbon chain length=4 (butane) if methylated at C1 becomes the C5 alkane pentane The mean BMACs are shown for all subjects, younger subjects and older subjects in, 3 and 4 respectively.
Figure 3:
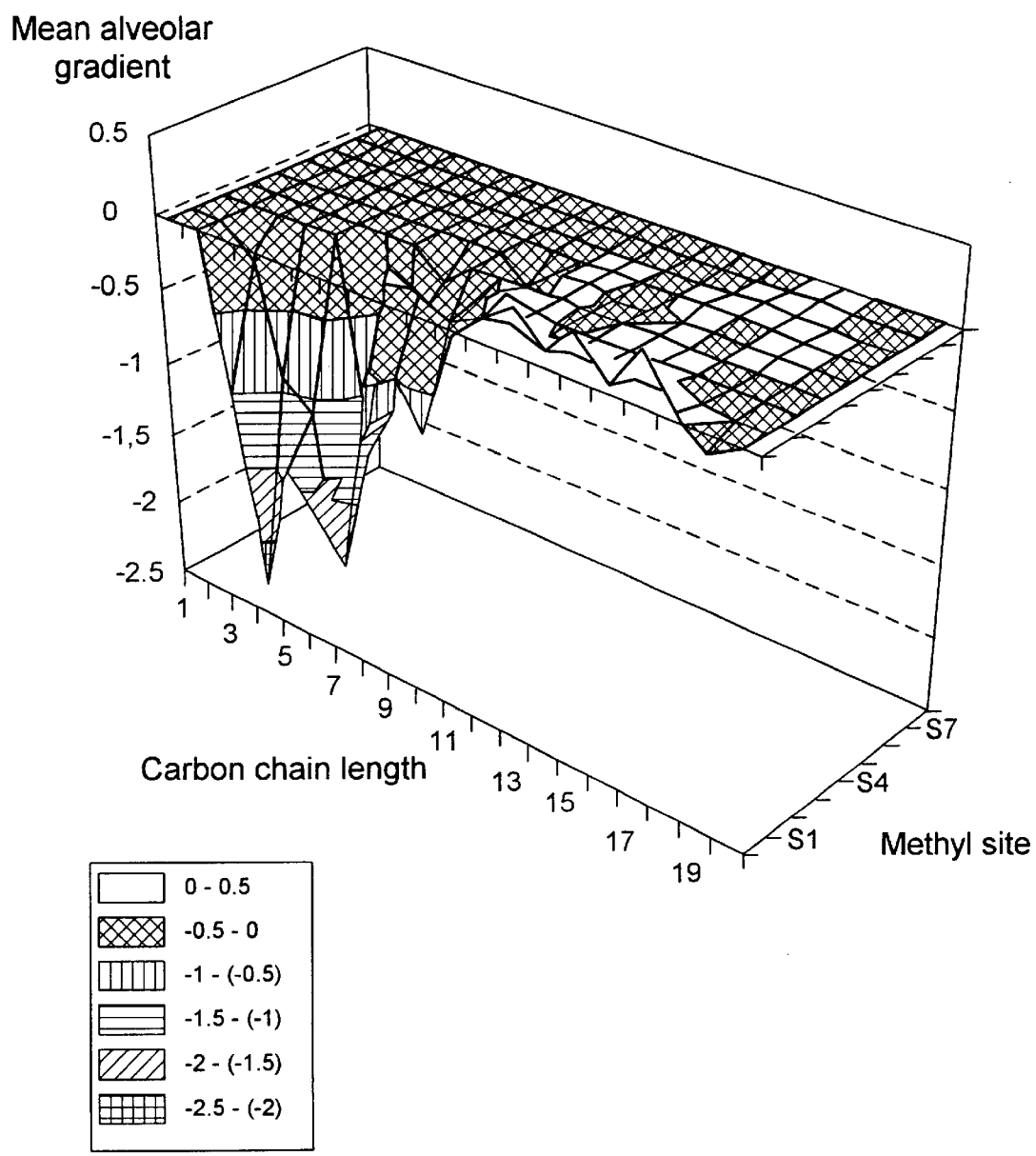
FIG. 3: Breath methylated alkane contour—mean of younger subjects. The mean BMAC of 49 normals aged 9 to 40 is shown.
Figure 4:
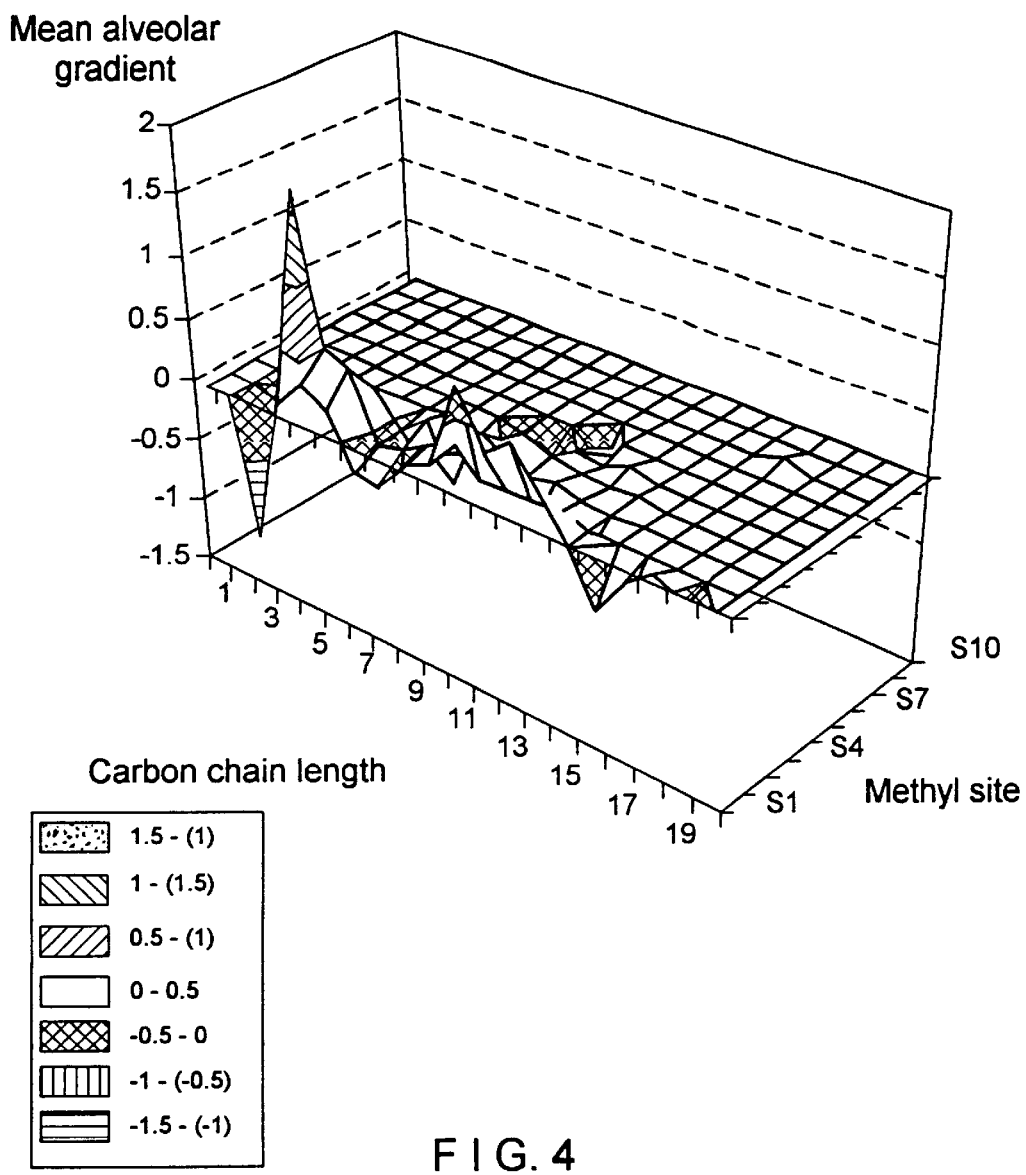
FIG. 4: Breath methylated alkane contour—mean of older subjects. The mean BMAC of 50 normals aged 40 to 89 is shown. Note that several peaks were elevated in comparison to the mean BMAC of the younger normals. 25 of these were statistically significant (see Table 1).

The mean BMACs are shown for all subjects, younger subjects and older subjects in FIGS. 2, 3 and 4 respectively. 25 of these VOCs were significantly different in the two groups (Table 1).

Figure 5:
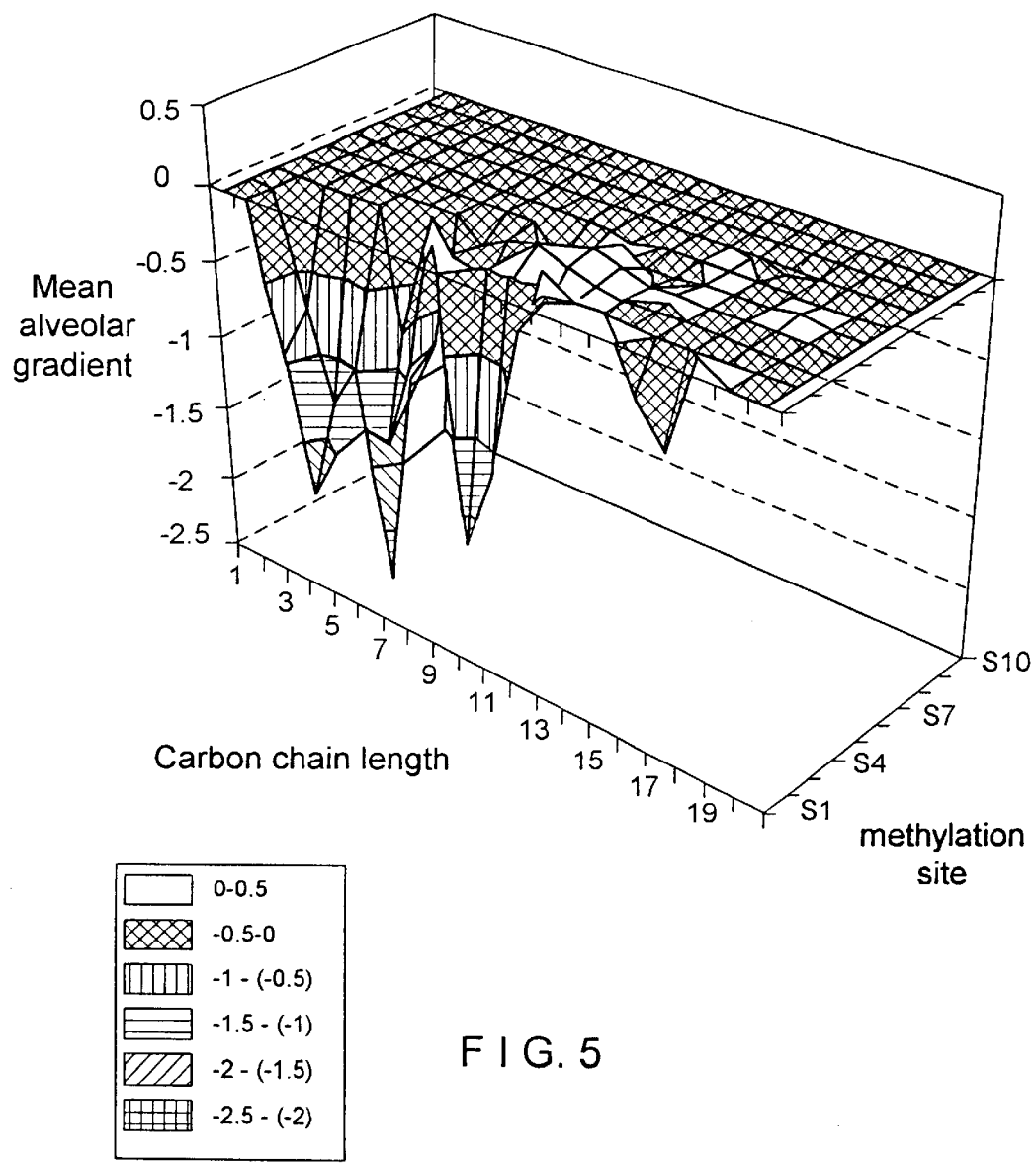
FIG. 5: Breath methylated alkane contour—mean of smokers. The mean BMAC of 11 smokers is shown.
Figure 6:
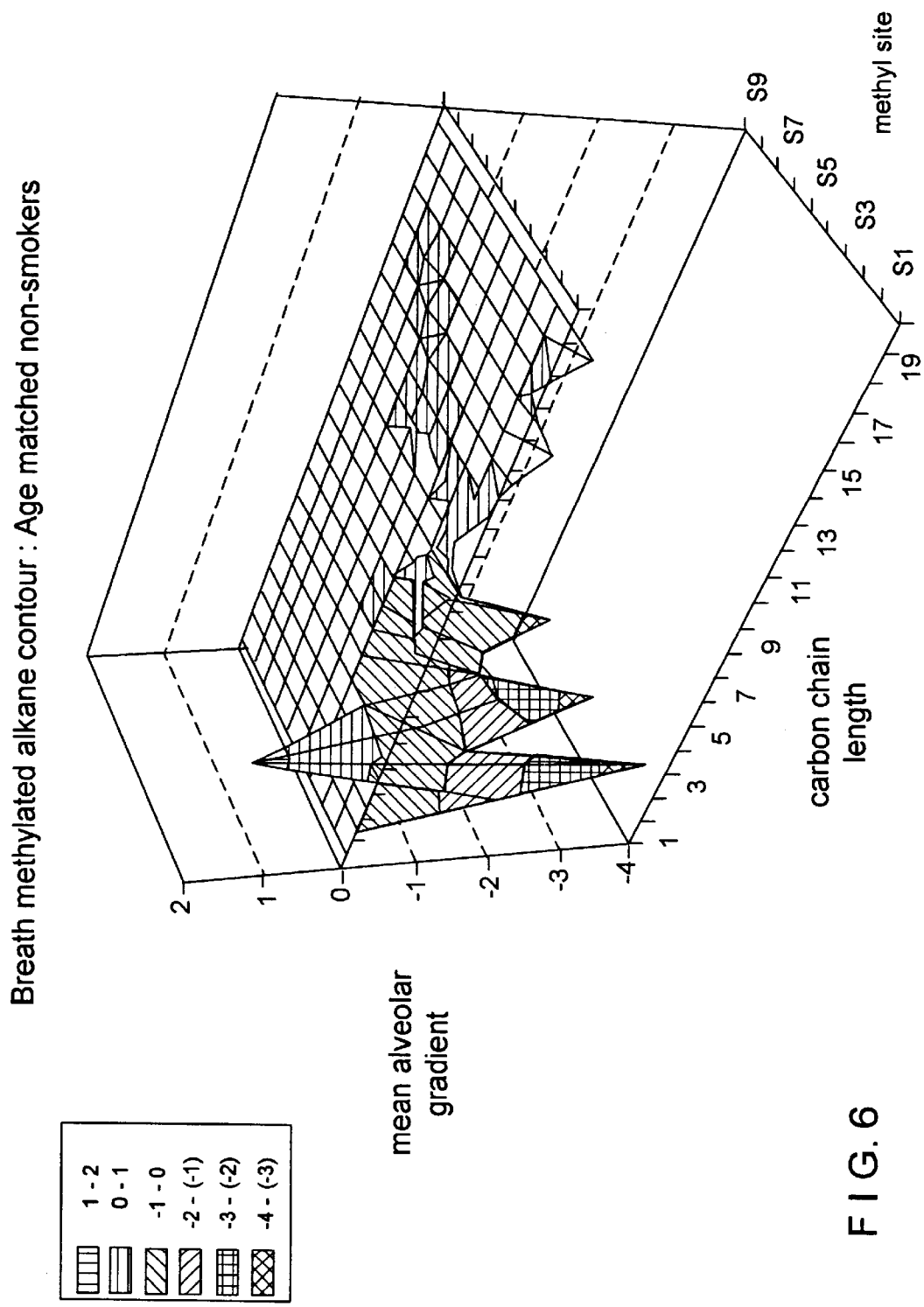
FIG. 6: Breath methylated alkane contour—mean of non-smokers. The mean BMAC of 11 non-smokers is shown, matched in age to the smokers shown in FIG. 5

Smokers (n=11) were compared to age matched non-smokers; their mean BMACs are shown in FIGS. 5 and 6 respectively. From the above, it was found that:

1. The BMAC was developed as a new marker of oxidative stress in humans.
2. The mean BMAC in normal humans varied with age: 25 species of alkanes and methylated alkanes were significantly different in older and younger subjects. Since most of the compounds were increased in the older subjects, these differences may have been due to
   a. an increase in oxidative stress with age, or
   b. a decrease in metabolism by cytochrome p450 enzymes with age, or
   c. a combination of a and b These findings were consistent with previous reports of increased oxidative stress and breath pentane concentrations with age in normal humans (18,19).
3. The mean BMAC in normal humans varied with smoking status. Compounds were both increased and decreased in the smokers, these differences were most likely due to a combination of:
   a. Increased clearance of alkanes and methylalkanes by cytochrome p450 enzymes induced smoking. This is consistent with previous reports that tobacco smoking is a potent inducer of cytochrome p450 enzymes (20–22).
   b. Increased oxidative stress with smoking, which is also likely in view of previous reports linking smoking with oxidative stress (23–25).

The Breath Methylated Alkane Contour in Heart Transplant Rejection

Testing for Oxidative Stress in Heart Transplant Rejection

More than 17,000 people now live with a transplanted heart in the United States (26). All of them require periodic screening for heart transplant rejection, but this condition is frequently difficult to detect. Clinical manifestations such as malaise, fatigue, dyspnea, edema, and anorexia are all relatively insensitive and non-specific; so too are noninvasive tests such as electrocardiography, echocardiography, thallium scintigraphy and magnetic resonance imaging. Hence, right ventricular endomyocardial biopsy remains the standard against which all other tests are compared (27–31). Endomyocardial biopsy is employed to identify allograft rejection or infection, and assess the efficacy of treatment. Post-operative biopsies are generally performed weekly for the first six weeks, biweekly until the third month, then monthly until the sixth month. Subsequent biopsies are scheduled on an individual basis. However, right ventricular endomyocardial biopsy is an invasive and comparatively expensive procedure which may result in complications including hematoma, infection, arrhythmia, ventricular perforation, and fistulas. This has stimulated research into alternative non-invasive tests for heart transplant rejection such as breath microanalysis (32).

Figure 7:
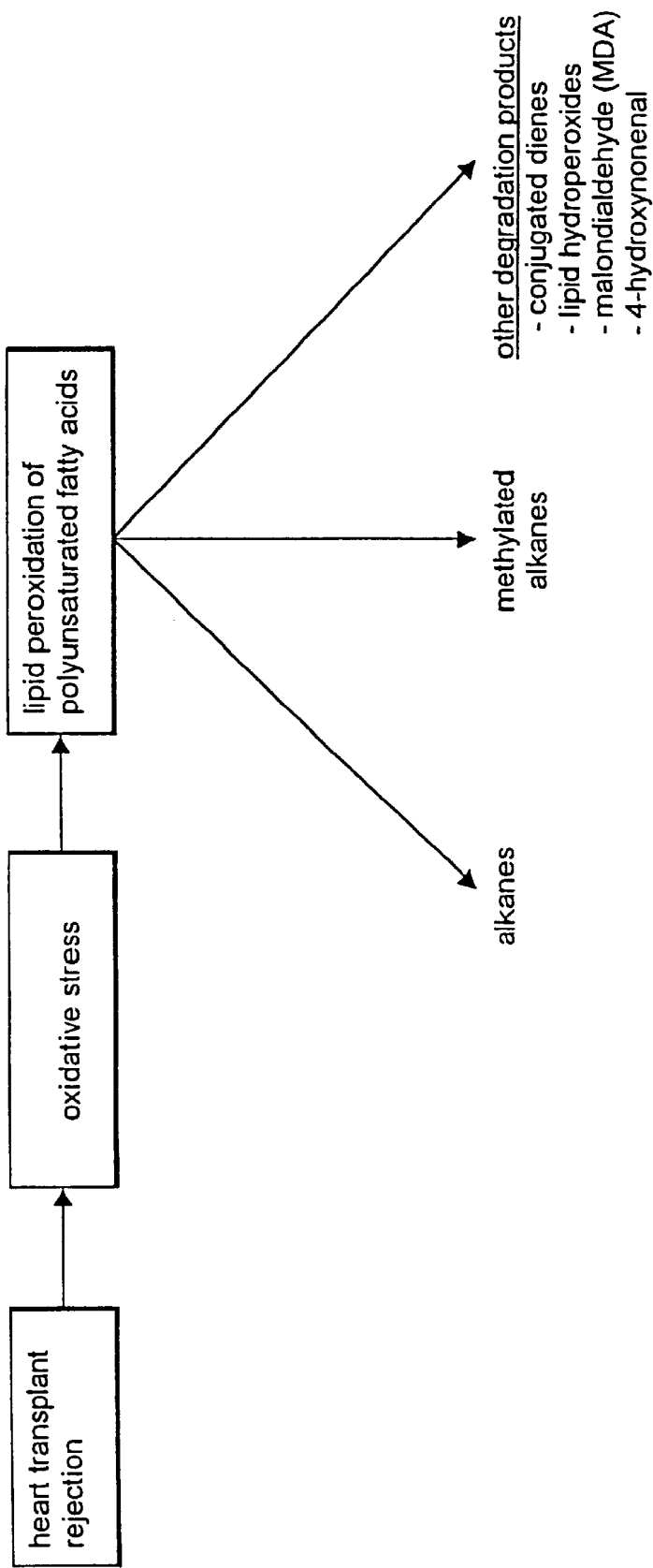
FIG. 7: Relationship between heart transplant rejection and VOCs in breath. Heart transplant rejection elicits the formation of reactive oxygen species (ROS) in the myocardium, which degrade polyunsaturated fatty acids (PUFAs) to alkanes and other degradation products. The origin of the methylated alkanes is unknown; possible pathways include degradation of PUFAs or methylation of alkanes. Alkanes and methylated alkanes are volatile organic compounds (VOCs) which are excreted in the breath.

Breath tests for heart transplant rejection are based on two observations: First, allograft rejection is accompanied by oxidative stress, due to the increased production of reactive oxygen species (ROS) in the myocardium (33, 34). Second, ROS degrade cellular membranes by lipid peroxidation of polyunsaturated fatty acids (PUFAs), evolving alkanes and alkane derivatives which are excreted in the breath as volatile organic compounds (VOCs) (35, 36) (FIG. 7). Animal studies have also demonstrated increased oxidative stress in allografts of heart and liver (37, 38). The resulting chemical and anatomical disruption of membranes may progress to cellular dysfunction and death. VOC's produced by this process include alkanes (e.g. pentane) and alkane derivatives which are excreted in the breath where they may provide clinically useful markers of oxidative stress. The breath methylated alkane contour (BMAC) was employed to study breath markers of rejection in heart transplant patients undergoing endomyocardial biopsy.

Material and Methods

Human subjects: Characteristics of the subject population are shown in Table 2. 210 technically satisfactory breath VOC samples were collected from heart transplant recipients on the same day as regular scheduled endomyocardial biopsy. Patients were studied at three sites: Newark Beth Israel Medical Center, Newark, N.J. (n=24), Mt. Sinai Medical Center, New York, N.Y. (n=37), and Columbia Presbyterian Medical Center, New York, N.Y. (n=149). Twenty (20) age-matched normal controls were selected from a data base of fasting normal subjects studied at the Sisters of Charity Medical Center, St. Vincent's Campus, Staten Island, N.Y. (14). The research was approved by the institutional review boards of all participating institutions.

Breath collection and assay: The method has been described (39, 40). In summary, a portable BCA was employed to capture the VOCs in 1.0 l breath onto a sorbent trap; VOCs in 1.0 l room air were captured on a separate sorbent trap. Subjects wore a nose clip while breathing in and out of the disposable mouthpiece of the BCA for 2.0 min. Light flap valves in the mouthpiece presented low resistance to respiration, and it was possible to collect breath samples without discomfort even from elderly patients and those suffering from pulmonary disease. All sorbent traps were sent to the laboratory for analysis of VOCs by ATD/GC/MS.

Grading of rejection: Endomyocardial biopsies were jointly evaluated by two pathologists who graded the degree of rejection employing a standard rating scale from 0 (no evidence of rejection) through Ia, Ib, II and IIIa (41).

Masking procedures: Sorbent traps were analyzed for VOCs in the laboratory by technical assistants who had no knowledge of the pathological findings. The pathologists reviewing the biopsies had no knowledge of the results of the breath test;

Analysis of data: All chromatograms of breath and air were automatically downloaded into computer-based spreadsheets, and then into a computer-based relational data base. The breath methylated alkane contour (BMAC) was determined in all subjects.

Results

Human subjects and endomyocardial biopsies: All human subjects recruited for the research were able to donate a breath sample into the BCA, and none reported any discomfort or adverse effects from the breath collection procedure. Two pathologists graded rejection in the endomyocardial biopsies: Grade 0 118/210, (56.2%), Ia 48/210 (22.9%), Ib 14/210 (6.7%),II 23/210 (10.9%) and IIIa 7/210 (3.3%). Only one of the age-matched normal controls and three of the transplant recipients were smokers, so the potential effects of smoking were not analyzed separately.

Figure 8:
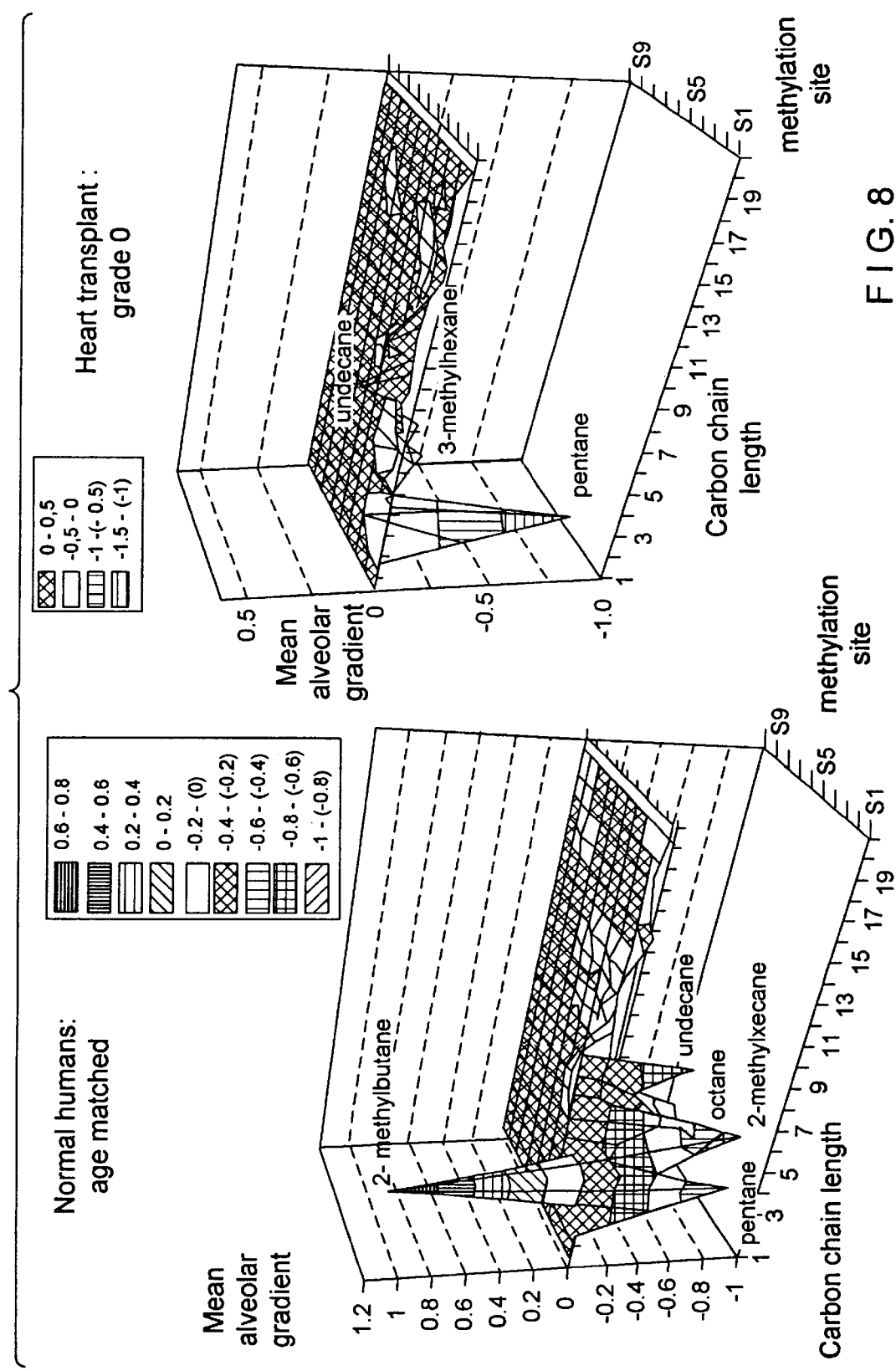
FIG. 8: Breath methylated alkane contour—Differences between transplant recipients and normals: The mean BMACs of heart transplant recipients with Grade 0 rejection (i.e. no histological evidence of rejection) and age-matched normal controls are shown. Note that a number of peaks which are strongly negative in the normals are not so apparent in the heart transplant recipients. VOCs which were significantly different are shown in Table 3.
Figure 9B:
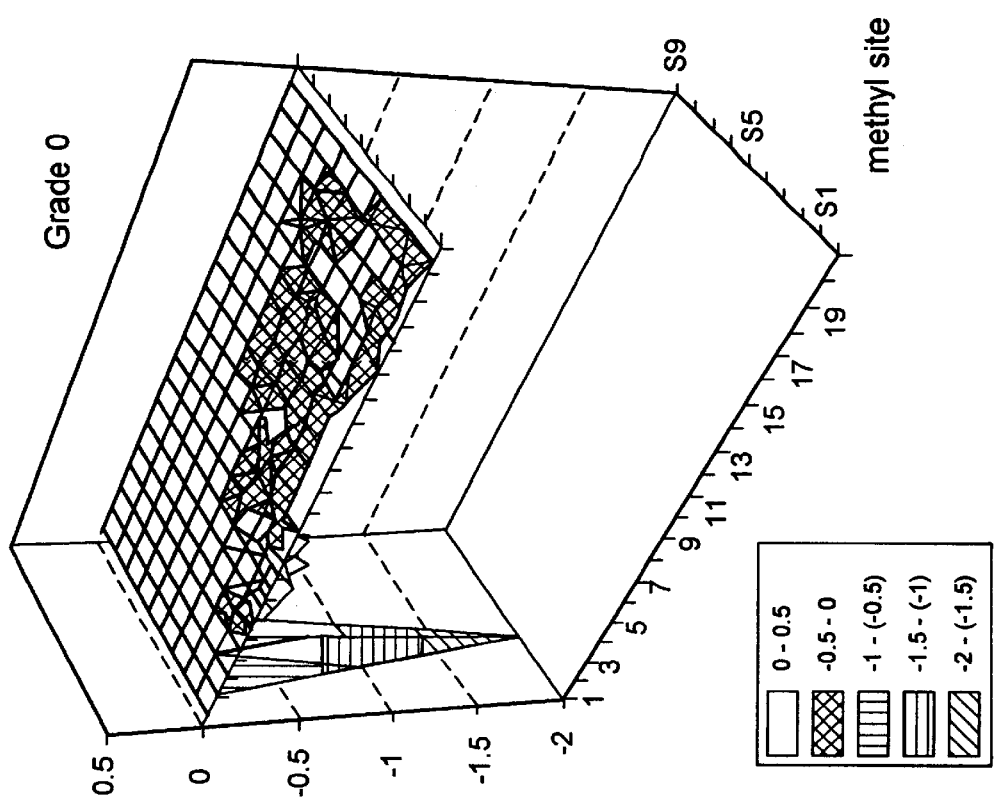
FIG. 9: Breath methylated alkane contour—Differences between heart transplant recipients with different grades of rejection: The mean BMACs of heart transplant recipients with Grade 0, Grade Ia and Ib, Grade II and Grade IIIa rejection are shown in FIG. 9, VOCs which were significantly different in patients with Grade 0 and Grade IIIa rejection are shown in Table 4.
Figure 9A:
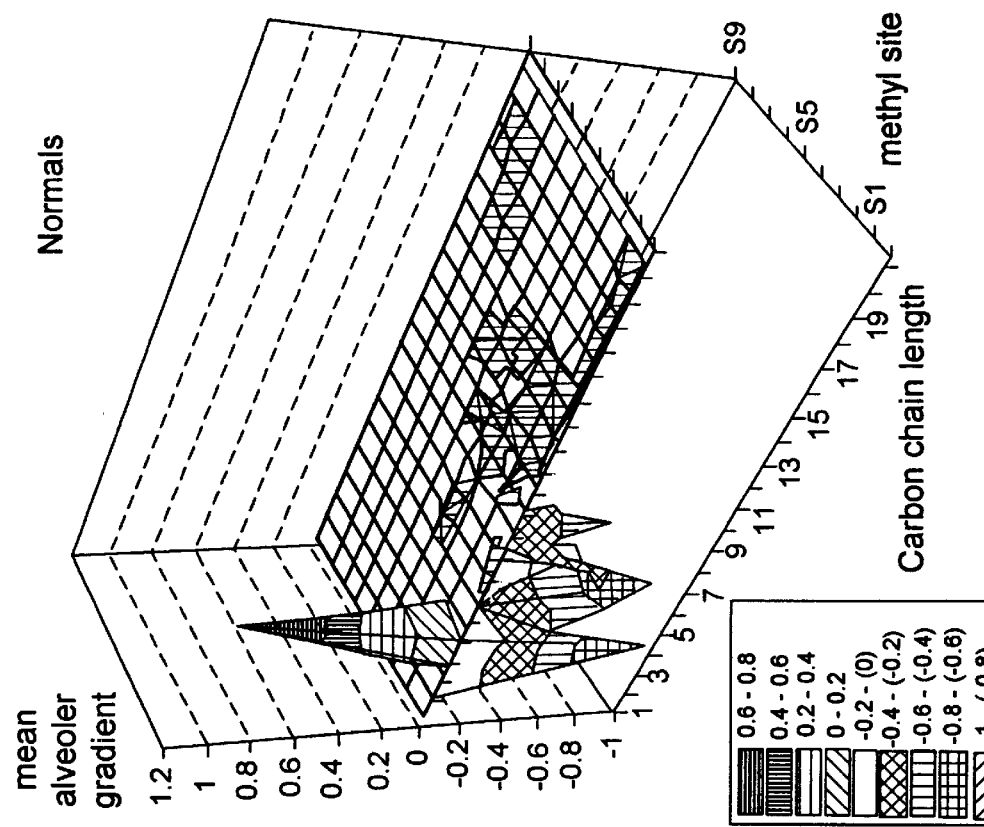
Figure 9D:
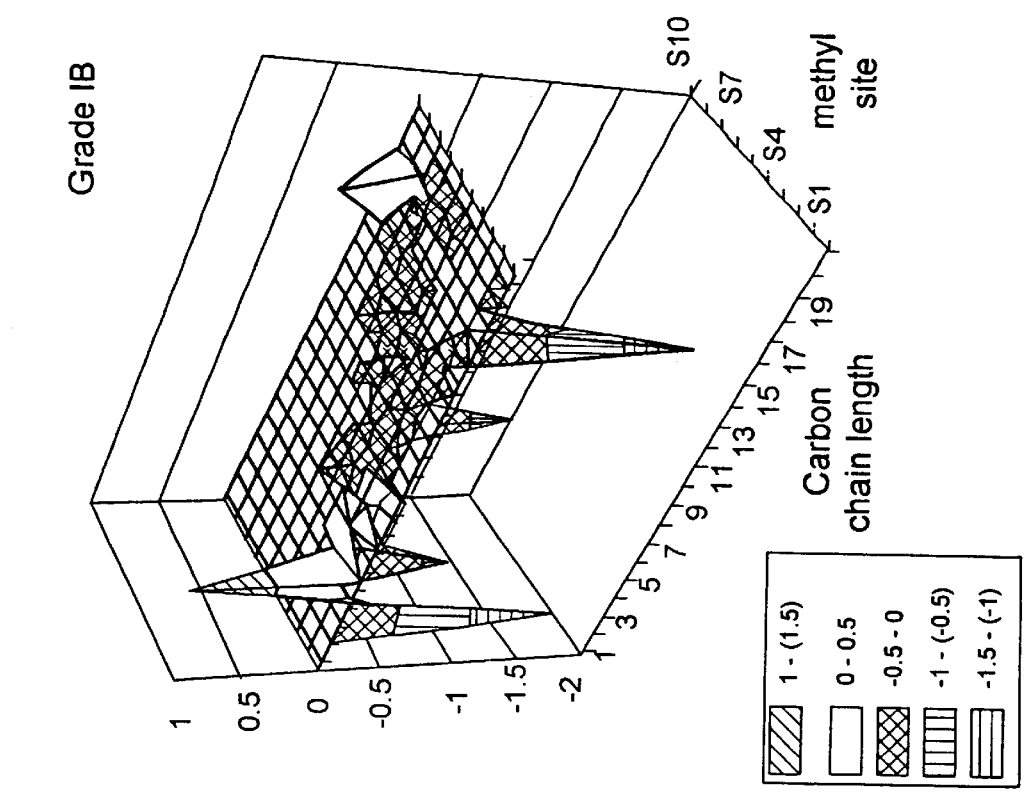
Figure 9C:
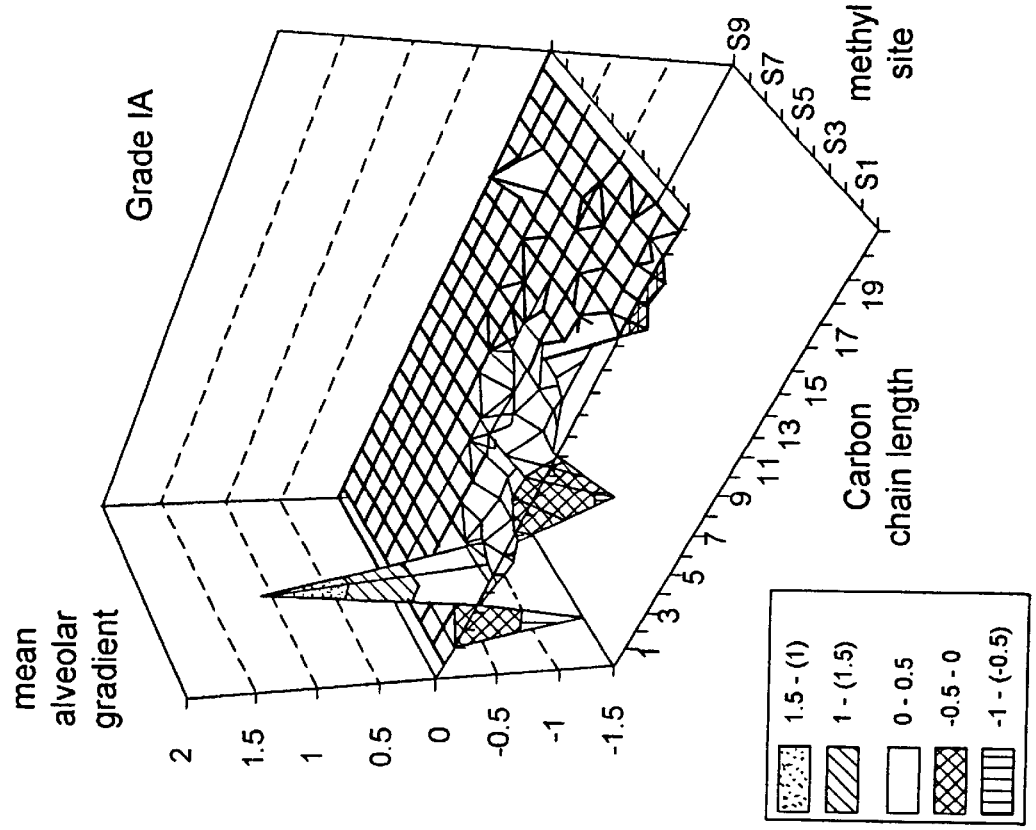
Figures 9E, 9F:
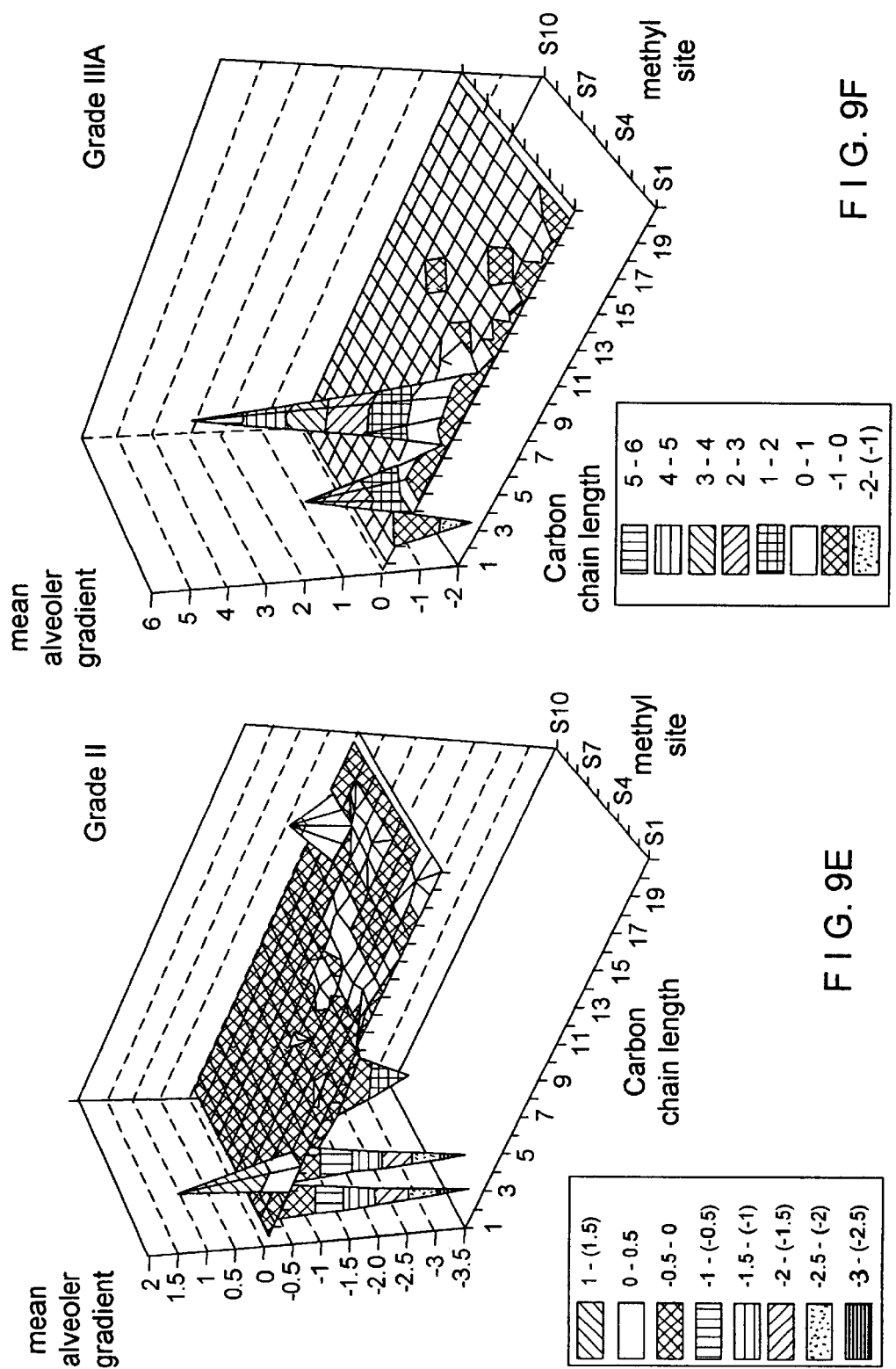

Breath VOCs: Differences between heart transplant recipients and normals: The mean BMACs of heart transplant recipients with Grade 0 rejection (i.e. no histological evidence of rejection) and age-matched normal controls are shown in FIG. 8 and Table 3.

Breath VOCs: Differences between heart transplant recipients with different grades of rejection: The mean BMACs of heart transplant recipients with Grade 0, Grade Ia and Ib, Grade II and Grade IIIa rejection are shown in FIG. 9 and Table 4.

Figure 10:
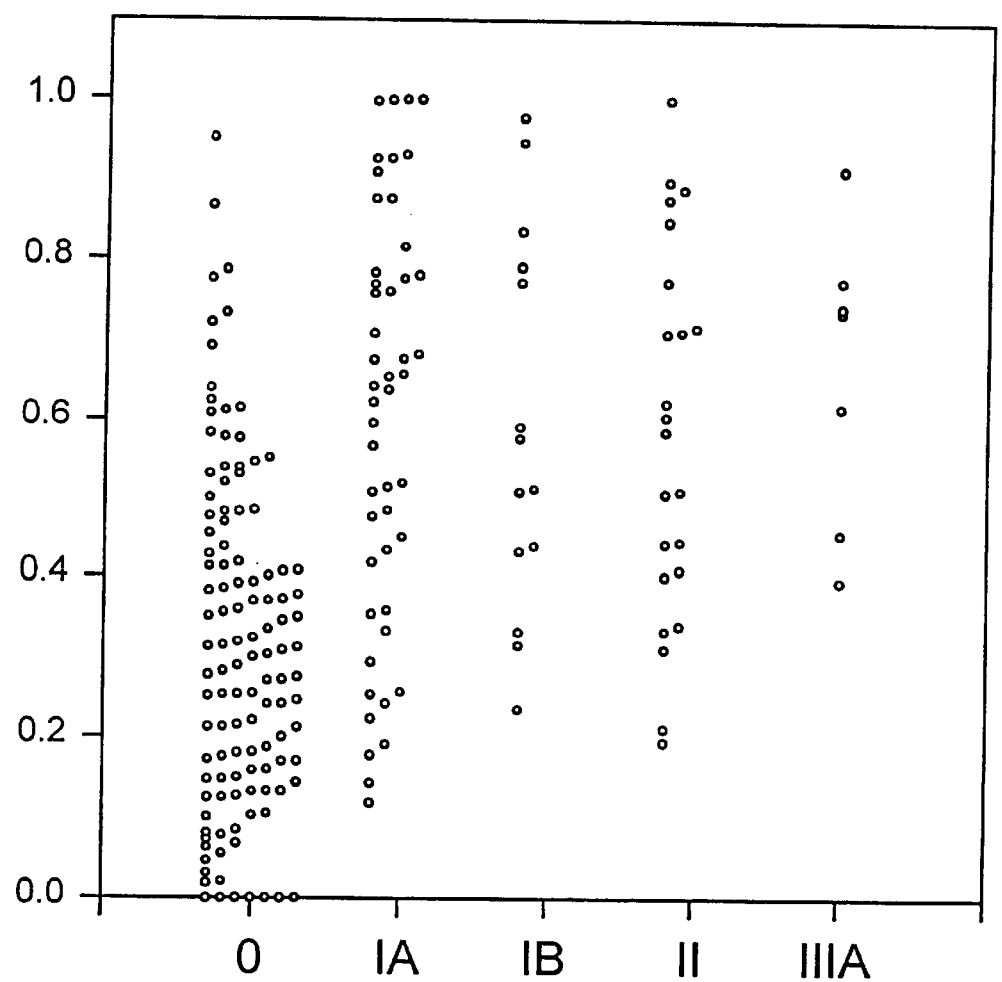
FIG. 10: Scatter diagram of the probability of rejection in all subjects. The probability of heart transplant rejection was determined by dividing the heart transplant recipients into two groups: those with no evidence of rejection (Grade 0) and those with any evidence of rejection (Grades Ia and Ib, II and IIIa). The BMACs of the patients in the two groups were compared by logistic regression, to generate a probability of rejection.
Figure 11:
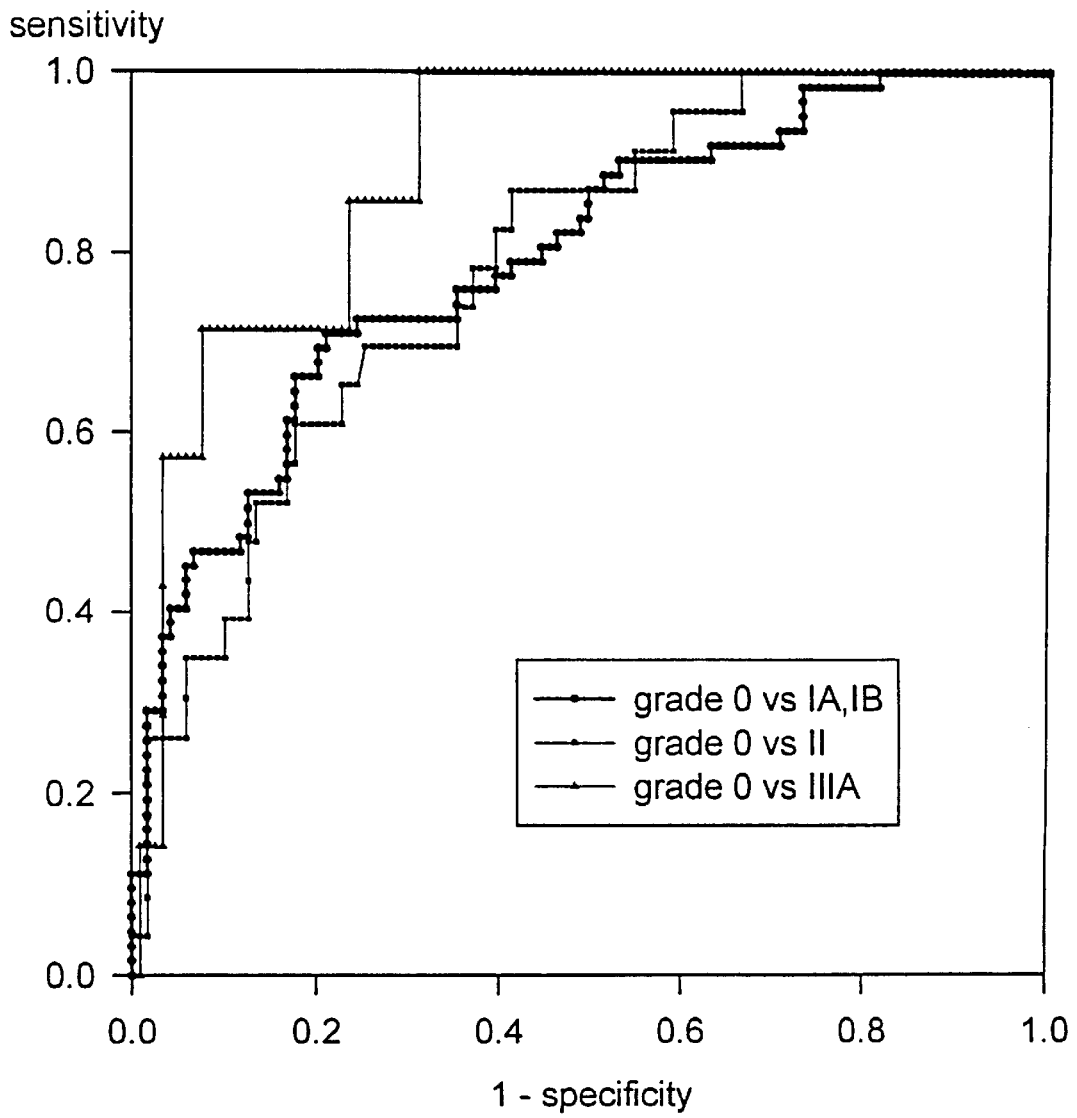
FIG. 11: Sensitivity and specificity of the breath test for heart transplant rejection: These receiver operating characteristic (ROC) curves were generated from the probabilities of rejection shown in FIG. 10. The test was most sensitive and specific for Grade IIIa rejection, and less so for Grades Ia, Ib, and II.

Determination of sensitivity and specificity: The BMACs were analyzed by logistic regression in order to compare the results of the breath test in heart transplant recipients with no evidence of rejection (Grade 0) to those with any evidence of rejection (Grades Ia, Ib, II and IIIa). The probability of heart transplant rejection was calculated for each patient, and displayed in a scatter diagram (FIG. 10). The sensitivity and specificity of the breath test was determined from these values (FIG. 11). The BMAC identified Grade IIIa rejection with 100% sensitivity and 68.6% specificity, Grade II rejection with 73.9% sensitivity and 64.4% specificity, and Grade Ia and Ib rejection with 75.8% sensitivity and 64.4% specificity.

From the results of the study, the following conclusions can be drawn:
1. Oxidative stress was greater in heart transplant recipients than in age-matched normal controls.
2. Oxidative stress increased with the severity of heart transplant rejection.
3. The breath test was sensitive and specific for clinically significant rejection.
1. Oxidative Stress Was Greater in Heart Transplant Recipients than in Age-matched Normal Controls.

Compared to age-matched normal controls, the BMAC was significantly elevated in heart transplant recipients who had no microscopic signs of rejection in their endomyocardial biopsy. The differences were qualitatively similar to the differences observed between normal non-smokers and smokers (FIGS. 5 and 6). This finding is consistent with an abnormally high level of oxidative stress in the transplanted heart, possibly resulting from chronic subclinical inflammation and/or rejection. Oxidative stress has been proposed as a risk factor for coronary artery disease, but the linkage has not been convincingly proven (42, 43). However, accelerated coronary artery disease is now the major cause of death in heart transplant recipients who have survived more than one year (44, 45), and increased oxidative stress may play a role in its development.

2. Oxidative Stress Increased with the Severity of Heart Transplant Rejection.

Coenzyme Q10 is depleted in transplanted human hearts, and mitochondrial respiratory chain function and energy production vary with the histological severity of rejection (46), so it is possible that increased oxidative stress might have been caused by impaired mitochondrial function.

3. The Breath Test was Sensitive and Specific for Clinically Significant Rejection.

In most heart transplant centers, only Grade III rejection is treated aggressively. The sensitivity and specificity of the breath test in in heart transplant recipients with Grade II and Grade III rejection was sufficiently high to serve as a screening test to identify those who required additional evaluation and treatment from those who did not. The test was noninvasive, safe, and highly acceptable to patients. Breath testing of heart transplant recipients could potentially reduce the number of endomyocardial biopsies performed every year, with a consequent reduction in patient morbidity and health-care costs.

The BMAC appears to provide a new and highly sensitive marker of oxidative stress. As such, it may have a role in a number of diseases for primary screening, as well as to monitor the efficacy of treatment. Based on previous studies, breath testing for the BMAC may be of potential clinical value in the detection and treatment of breast cancer, lung cancer, ischemic heart disease, and kidney disease, though this is not intended as an exclusive list.

TABLES

Table 1: Alkanes and methylalkanes significantly increased in older normals: 2-tailed t-tests comparing the compounds shown in FIGS. 3 and 4, demonstrating the statistical significance of the differences between younger and older normal humans.

Table 2: Characteristics of subject population. A number of the heart transplant recipients were studied more than once, on different occasions at least one month apart. There was no significant difference between the ages of the heart transplant recipients and the normal controls.

Table 3: Alkanes and methylalkanes in heart transplant recipients: Grade 0 rejection versus age-matched normal controls. 2-tailed t-tests were employed to compare the compounds shown in FIG. 8 demonstrating the statistical significance of the differences between heart transplant recipients with Grade 0 rejection and age-matched normal controls.

Table 4: Alkanes and methylalkanes in heart transplant recipients: Grade IIIa rejection versus Grade 0 rejection. 2-tailed t-tests were employed to compare the compounds shown in FIG. 9 demonstrating the statistical significance of the differences between heart transplant recipients with Grade IIIa rejection compared to those with Grade 0 rejection.

TABLE 1

Alkanes and methylalkanes significantly increased in older normals $p < 0.00001$ decane, 3-methyl
heptane, 3-methyl
$p < 0.0001$ dodecane, 6-methyl
heptane
octane
heptane, 2-methyl TABLE 1-continued Alkanes and methylalkanes significantly increased in older normals octane, 3-methyl
hexane, 3-methyl
hexane, 2-methyl
$p < 0.001$ decane, 2-methyl
nonane, 2-methyl
hexane
decane, 5-methyl
$p < 0.01$ nonane
tetradecane, 5-methyl
undecane, 5-methyl
undecane
tridecane, 3-methyl
$p < 0.05$ octane, 4-methyl
heptadecane
pentane, 2-methyl
decane
octane, 2-methyl
butane, 2-methyl
dodecane

TABLE 2

Characteristics of subjects

|  | Normal controls | Heart transplant recipients |
| --- | --- | --- |
| Total no. | 20 | 126 |
| no. breath samples | 20 | 210 |
| no. endomyocardial biopsies | — | 210 |
| Mean age (SD) |  |  |
| Males | 50.6 (9.9) | 52.3 (12.0) |
| Females | 50.4 (12.3) | 54.9 (9.33) |
| Sex (m/f) | 12/8 | 107/19 |

TABLE 3

Alkanes and methylalkanes significantly increased in heart transplant recipients VOCs are ranked in decreasing order of statistical significance
($p < 0.05$ for all, on 2-tailed t-test)
decane, 5-methyl
eicosane, 3-methyl
heptane, 2-methyl
heptane, 3-methyl
hexane, 2-methyl
nonadecane, 3-methyl
nonane, 5-methyl
octane, 3-methyl
pentane, 3-methyl
tetradecane, 3-methyl
heptane
hexane
octane
tetradecane

TABLE 4

Alkanes and methylalkanes in heart transplant recipients: Grade IIIa rejection versus Grade 0 rejection.

VOCs are ranked in decreasing order of statistical significance ($p < 0.05$ for all, on 2-tailed t-test)
heptadecane, 3-methyl
heptadecane, 7-methyl
octadecane, 2-methyl
octadecane, 5-methyl
pentadecane, 5-methyl
tetradecane, 4-methyl
tridecane, 4-methyl

References

1. Fridovich I. The biology of oxygen radicals. Science 201:875–880; 1978
2. Pryor W A: Measurement of oxidative stress status in humans. Cancer Epidemiol Biomarkers Prev 2(3):289–292; 1993
3. Ashok B T; Ali R: The aging paradox: free radical theory of aging Exp Gerontol 1999 34(3):293–303
4. Saretzki G and von Zglinicki T: (Replicative senescence as a model of aging: the role of oxidative stress and telomere shortening—an overview) Z Gerontol Geriatr 1999;32(2):69–75
5. Halliwell B, Gutteridge J M C, Cross C E: Free radicals, antioxidants, and human disease: Where are we now? J Lab Clin Med 119: 598–620;1992
6. Kneepkens C M F, Ferreira C, Lepage G and Roy C C: The hydrocarbon breath test in the study of lipid peroxidation: principles and practice. Clin Invest Med 1992; 15(2):163–186.
7. Kneepkens C M F, Lepage G, Roy C C. The potential of the hydrocarbon breath test as a measure of lipid peroxidation. Free Radic Biol Med 1994;17:127–60.
8. Phillips M: Breath tests in medicine. Scientific American 1992;267(1):74–79.
9. Hietanen E, Bartsch H, Bereziat J-C, Camus A-M, McClinton S, Eremin 0, Davidson L and Boyle P: Diet and oxidative stress in breast, colon and prostate cancer patients: a case control study. European Journal of Clinical Nutrition 48:575–586; 1994
10. Humad S, Zarling E, Clapper M and Skosey J L: Breath pentane excretion as a marker of disease activity in rheumatoid arthritis. Free Rad Res Comms 5(2):101–106;1988
11. Sobotka P A, Gupta D K, Lansky D M, Costanzo M R and Zarling E J: Breath pentane is a marker of acute cardiac allograft rejection. J Heart Lung Transplant 13:224–9;1994
12. Weitz Z W, Birnbaum A J, Sobotka P A, Zarling E J and Skosey J L: High breath pentane concentrations during acute myocardial infarction. Lancet 337:933–35;1991
13. Kovaleva E. S, Orlov O. N, Tsutsulkovskaia Mia, Vladimirova T. V, Beliaev B. S: Lipid peroxidation processes in patients with schizophrenia. Zh Nevropatol Psikiatr 89(5): 108–10; 1989
14. Olopade C O, Zakkar M, Swedler W I and Rubinstein I: Exhaled pentane levels in acute asthma. Chest 111(4):862–5; 1997
15. Phillips M, Herrera J, Krishnan S, Zain M, Greenberg J and Cataneo R N: Variation in volatile organic compounds in the breath of normal humans. Journal of Chromatography B 629(1–2):75–88; 1999
16. Phillips M, Gleeson K, Hughes J M B, Greenberg J, Cataneo R N, Baker L and McVay W P: Volatile organic compounds in breath as markers of lung cancer: a cross-sectional study. Lancet 353:1930–33; 1999
17. Phillips M: Method for the collection and assay of volatile organic compounds in breath. Analytical Biochemistry 247: 272–278; 1997
18. Zarling E J, Mobarhan S, Bowen P and Kamath S: Pulmonary pentane excretion increases with age in healthy subjects. Mech Ageing Dev 67(1–2): 141–7; 1993
19. Jones M, Shiel N, Summan M, Sharer N M, Hambleton G, Super M and Braganza J M: Application of breath pentane analysis to monitor age-related change in free radical activity. Biochem Soc Trans 21(4): 485S; 1993
20. Zevin S and Benowitz N L: Drug interactions with tobacco smoking. An update. Clin Pharmacokinet 1999 36(6):425–38.
21. Pasanen M and Pelkonen 0: The expression and environmental regulation of P450 enzymes in human placenta. Crit Rev Toxicol 1994;24(3):211–29
22. Nebert D W, Petersen D D and Puga A: Human AH locus polymorphism and cancer: inducibility of CYP1A1 and other genes by combustion products and dioxin. Pharmacogenetics 1991;1(2):68–78
23. Kalra J, Chaudhary A K and Prasad K: Increased production of oxygen free radicals in cigarette smokers. Int J Exp Pathol 1991;72(1):1–7
24. Bridges A B, Scott N A, Parry G J and Belch J J: Age, sex, cigarette smoking and indices of free radical activity in healthy humans. Eur J Med 1993;2(4):205–8
25. Church D F and Pryor W A: Free-radical chemistry of cigarette smoke and its toxicological implications. Environ Health Perspect 1985;64:111–26
26. Source: United Network for Organ Sharing, Richmond, Va. Scientific Registry data.
27. Hosenpud J D: Noninvasive diagnosis of cardiac allograft rejection. Circulation 1991 ;85:368
28. Duquesnoy R J, Demetris A J: Immunopathology of cardiac transplant rejection. Curr Opinion Cardiol 1995; 10:155
29. Winters G L: The pathology of heart allograft rejection. Arch Pathol Lab Med 1991; 115:226
30. Caves B C, Billingham M E, Stinson E B and Shumway N E: Serial transvenous biopsy of the transplanted human heart: improved management of acute rejection episodes. Lancet 1974;1:821
31. Winters G L, Loh E, Schoen F J: Natural history of focal moderate cardiac allograft rejection, Circulation 1995;91:1975.
32. Sobotka P A, Gupta D K, Lansky D M, Costanzo M R and Zarling E J: Breath pentane is a marker of acute cardiac allograft rejection. J Heart Lung Transplant 1994; 13:224–9.
33. Coles J G; Romaschin A D; Wilson G J; Mickle D A; Dasmahapatra H; Martell M; Mehra A; Tsao P: Oxygen free radical-mediated lipid peroxidation injury in acute cardiac allograft rejection. Transplantation 1992; 54(1): 175–8
34. Roza A M; Pieper G; Moore-Hilton G; Johnson C P; Adams M B: Free radicals in pancreatic and cardiac allograft rejection. Transplant Proc 1994 26(2):544–5
35. Kneepkens C M F, Ferreira C, Lepage G and Roy C C: The hydrocarbon breath test in the study of lipid peroxidation: principles and practice. Clin Invest Med 1992; 15(2):163–186.
36. Kneepkens C M F, Lepage G, Roy C C. The potential of the hydrocarbon breath test as a measure of lipid peroxidation. Free Radic Biol Med 1994;17:127–60.
37. Kuo P C; Alfrey E J; Krieger N R; Abe K Y; Huie P; Sibley R K; Dafoe D C: Differential localization of allograft nitric oxide synthesis: comparison of liver and heart transplantation in the rat model. Immunology 1996 Apr;87(4):647–53
38. Winlaw D S; Schyvens C G; Smythe G A; Du Zy; Rainer S P; Keogh A M; Mundy J A; Lord R S; Spratt P M; MacDonald P S: Urinary nitrate excretion is a noninvasive indicator of acute cardiac allograft rejection and nitric oxide production in the rat. Transplantation 1994 Nov. 20 15;58(9):1031–6
39. Phillips M, Herrera J, Krishnan S, Zain M, Greenberg J and Cataneo R N: Variation in volatile organic compounds in the breath of normal humans. Journal of Chromatography B 629(1–2):75–88; 1999
40. Phillips M: Method for the collection and assay of volatile organic compounds in breath. Analytical Biochemistry 247: 272–278; 1997
41. Billingham M E, Cary N R B, Hammond E H et al: A working formulation for the standardization of nomenclature in the diagnosis of heart and lung rejection. Heart rejection study group. Heart Transplant 1990;9:587.
42. Runge M S: The role of oxidative stress in atherosclerosis: the hope and the hype. Trans Am Clin Climatol Assoc 1999; 110:119–29
43. Hoeschen R J: Oxidative stress and cardiovascular disease. Can J Cardiol 1997; 13(11):1021–5
44. Radovancevic B and Frazier O H: Heart transplantation: approaching a new century. Tex Heart Inst J 1999;26(1):60–70
45. Deng M C, Tjan T D, Asfour B, Roeder N and Scheld H H: Transplant vasculopathy. Herz 1998;23(3): 197–201
46. Gvozdjakova A, Kucharska J, Mizera S, Braunova Z, Schreinerova Z, Schramekova E, Pechan I and Fabian J: Coenzyme Q10 depletion and mitochondrial energy disturbances in rejection development in patients after heart transplantation. Biofactors 1999;9(2–4):301–6.

I claim:

1. A process for determining the presence or absence of disease in a mammal, including a human, which comprises:

collecting a representative sample of alveolar breath from the mammal;

collecting a representative sample of ambient air;

analyzing the samples of breath and air to determine content of n-alkanes having 2 to 20 carbon atoms, inclusive analyzing the samples of breath and air to determine the methylation site, if any, of n-alkanes having 3 to 20 carbon atoms, inclusive;

calculating the alveolar gradients of the n-alkanes having 2 to 20 carbon atoms, inclusive, in the breath sample in order to determine a first component of the alkane profile;

calculating the alveolar gradients of methylated alkanes having 3 to 20 carbon atoms, inclusive, in the breath sample in order to determine a second component the alkane profile and comparing the alkane profile to baseline alkane profiles calculated for mammals known to be free of the disease to be determined;

the finding of differences in the alkane profile from the baseline alkane profile being indicative of the presence of the disease.

2. The method of claim 1 wherein the disease is heart transplant rejection.

* * * * *